United States Patent [19]

Ecanow

[11] 4,452,780
[45] Jun. 5, 1984

[54] COACERVATED IODINE

[75] Inventor: Charles S. Ecanow, Skokie, Ill.

[73] Assignee: NeoMed Corporation, Wilmette, Ill.

[21] Appl. No.: 451,467

[22] Filed: Feb. 25, 1983

Related U.S. Application Data

[63] Continuation-in-part of Ser. No. 258,050, Apr. 28, 1981, abandoned.

[51] Int. Cl.$^3$ ...................... A01N 59/12; A61K 33/22
[52] U.S. Cl. .................................................... 424/150
[58] Field of Search ........................................ 424/150

[56] References Cited

U.S. PATENT DOCUMENTS 4,088,597  5/1978  Morlock et al. .................... 424/150

OTHER PUBLICATIONS

Chemical Abstracts, vol. 83, (1975).

Primary Examiner—Elbert L. Roberts
Attorney, Agent, or Firm—Edward A. Ptacek

[57] ABSTRACT

A composition of matter possessing powerful germicidal, antiseptic, fungicidal and bacteriacidal properties and a method of preparing the same are disclosed. The claimed method of manufacture permits the incorporation of iodine, urea or an iodophore or any combination thereof in the lipoidal, non polar, liquid aqueous phase of a two phase liquid aqueous system thereby producing the said composition of matter. The claimed composition can be prepared across a range of pH values extending from 3.4 to 7.5 without any significant loss of stability or germicidal, antiseptic, fungicidal and bacteriacidal activity.

8 Claims, No Drawings

COACERVATED IODINE

This is a continuation-in-part of my co-pending application Ser. No. 258,050 filed Apr. 28, 1981 now abandoned.

BACKGROUND

Iodine based preparations are commonly acknowledged to be among the most effective of the available germicides and antiseptics. Moreover, solutions of iodine have been shown to have fungicidal and viricidal properties. It is also known that solutions of iodine appear to exhibit no selectivity against different strains of bacteria, all types being killed at approximately the same level of concentration and exposure time.

Numerous mixtures of iodine are now commercially available. These include iodoform, tincture of iodine, iodine trichloride and the various iodophores. Of the available embodiments of iodine, the iodophores are in most common use and presently occupy the position of greatest commercial interest.

The prior art teaches that crystalline iodine can be placed in solution through the use of surfactants such as polyvinyl-pyrrolidone, polyethoxyehanol derivatives and a variety of quaternary ammonium compounds. These resulting mixtures of iodine and surface active agents are referred to in the scientific literature as iodophores.

Iodophore solutions are polar and micellar in character. Given that iodine is highly insoluble in polar water, the problem of solubilizing iodine is partially solved in the preparation of iodophores by incorporating the iodine component in a micellar system. In effect, in iodophores, the iodine is solubilized and carried in micellar agregates which aggregates are formed through the use of surfactants such as those referred to above. The micellar system acts as a reservoir which liberates iodine into the polar water of the preparation and thence onto the surface to be treated.

Repeated studies have shown that iodophores exhibit maximum stability and activity in solutions, the pH of which must be within the range of 3.0 to 4.0. Solutions outside of this range consistently demonstrate reduced stability and germicidal activity. This restriction is commonly acknowledged to be among the shortcomings of the iodophores.

Investigation of the commercially available iodophores indicates that the inherent instability of iodine in polar water is not remedied through incorporation of that agent in micellar structures. On analysis, iodophore preparations are found to be complexes of a variety components; that is, they are comprised of mixtures of all possible oxidative states of iodine. Thus, when iodophores are evaporated to dryness, it is found that the compositions individual components, i.e. free iodine, free salts and surfactants are released onto the treated surface.

When, as in the claimed invention, iodophores or iodine is combined with the coacervate phase (the lipoidal non polar liquid aqueous phase) of the two phase liquid aqueous system of this invention, the defects described immediately above are eliminated.

OBJECTS

It is an object of this invention to disclose a unique method of manufacturing coacervated iodine. It is a further object to prepare coacervated compositions of iodine, iodophore or urea or combinations thereof and in so doing produce a series of antiseptics and germicides which are pharmaceutically active and in addition, stable across a range of pH values extending from 3.4 to 7.5. Additional objects will appear self evident from the following disclosure.

THE INVENTION

The prior art discloses that in the preparation of currently available iodophores, surfactants are used to directly solubilize crystalline iodine. The solubilized iodine is then embodied in a micellar, polar water medium. The claimed invention makes a distinctly different use of the surfactant agent. Instead of being used to directly solubilize iodine, it is used to prepare a two phase liquid aqueous system; said system being comprised of an equilibrium water phase and a lipoidal, non polar, liquid aqueous phase. In this invention, it is the lipoidal non polar liquid aqueous phase which is used to dissolve the iodine, iodophores, urea or mixtures thereof.

In the disclosed embodiment, the surface active agent binds and organizes the water of the composition. As such, it constitutes an integral part of an aqueous matrix which is insoluble in normal polar bulk water. It is evident then that the solvent system employed in this invention is fundamentally different from that used in the preparation of iodophores.

There is a further fundamental distinction between the claimed invention and the presently available iodophores. The disclosed method of manufacture produces a dissolution of the germicidal agent (i.e. iodine, iodophores, urea or mixtures thereof) whereas the manufacture of iodophores is based upon a solubilization of the germicidal agent, i.e. iodine. Solubilization produces a dispersion of iodine within the micelles of the solution, thereby creating iodine complexes which are soluble in bulk water. In the claimed composition, dissolution rather than solubilization occurs; in consequence, the germicidal agent(s) used, is dispersed throughout the solution. The process described immediately above produces a stable solution of dispersed molecules of the germicidal agent (i.e. iodine, iodophore, urea or combinations thereof), the precipitation of which is highly improbable.

It is evident from the described mode of manufacture of the claimed composition, that the total reservoir of the incorporated active agent (i.e. iodine, iodophore, urea etc) is continuously available to the surface being treated. If the claimed composition(s) is subjected to drying, it will evaporate to a gel. The resultant gel will maintain its structure as well as its antiseptic, bacteriacidal, germicidal, fungicidal and viricidal properties indefinitely. The component ingredients of the composition will remain essentially unchanged. In contrast, when iodophore preparations are subjected to drying, they will dry to a powder with consequent liberation of free iodine, free salts and surfactant and reduction of its germicidal effectiveness.

Because of its coacervate structure, the claimed composition differs in other respects from the presently available iodophores. First, its vapor pressures are lower than those of iodophores; consequently, it is significantly more stable than these latter preparations. In addition, the interfacial tensions of the claimed composition are approximately ½ dyne. This contrasts with the vapor pressures of iodophores which are not less than 29 dynes per cm. It follows from these facts that the wettability of the claimed composition; i.e. its ability to make and maintain contact with contiguous surfaces is clearly superior to that of known iodophores. In addition, because of the coacervate structure of the disclosed composition(s), on application to the surface to be treated, it will form a film which permits oxygen to diffuse to the said surface. Thus, aside from the intrinsic germicidal effect of the claimed composition, the fact that it permits the diffusion of oxygen to the affected surface means that anaerobic organism growth will be adversely affected and possibly prevented.

Unlike the presently available iodophores which must be manufactured within a pH range of 3.0 to 4.0, the claimed composition(s) can be prepared in embodiments which can range from 3.4 to 7.5 without any loss of stability or effectiveness. This feature not only distinguishes the disclosed invention from the known iodophores but constitutes an important advantage in that the claimed composition(s) can be readily prepared to a pH identical to that of human or animal fluids and tissues.

As previously described, the lipoidal non polar phase of the two phase coacervate system is used to dissolve the germicidal agent. Since this phase is comprised chiefly of water, the composition of which it is a part has all of the advantages of a water solvent. Thus, any of the embodiments of the claimed invention, when used as directed are free of toxic and irritating effects.

Regardless of which of the claimed methods are used to prepare the disclosed compositions, all of the described embodiments are effective antiseptic, bacteriacidal, germicidal, fungicidal and viricidal preparations. Further, absorption of the various embodiments of this invention onto surfaces such as bandages will not affect their effectiveness.

Using standardized, well known manufacturing processes, the claimed composition(s) can be prepared in all of the regular dosage forms; i.e. solutions, foams gels, ointments, suspensions, emulsions and detergents. Through microencapsulation procedures, powdered forms of the claimed composition(s) can be prepared. While the disclosed composition(s) can be used to disinfect or sterilize skin and most mucous membrane surfaces, introduction of these preparations into the eye is not recommended.

The prior art teaches that surfactants can be directly substituted for alchohol to solubilize iodine. However, the prior art does not suggest that the coacervate phase of a two phase liquid aqueous system can be used to dissolve (as opposed to solubilize) crystalline iodine, iodophore preparations or urea. Further, the prior art does not disclose that the use of said coacervate phase as described in this disclosure will endow the proposed compositions of matter with those thermodynamic, vapor pressures, interfacial tensions and other features considered desireable in compositions designed to have antiseptic, germicidal, fungicidal, bacteriacidal and viricidal effects.

The present disclosure does not claim originality regarding the concept of coacervate systems. What this disclosure does claim as original is its discovery of a manufacturing process which embodies one phase of a coacervate system and yields a composition of matter with superior antiseptic, germicidal, bacteriacidal, fungicidal and viricidal properties. Further, it is claimed that the use of a coacervate system as disclosed herein not only distinguishs it from the methods used to prepare iodophores but further, distinguishes the claimed composition(s) from all available iodophores and similar products.

DETAILED DESCRIPTION OF THE INVENTION

A number of non-toxic surfactant agents such as benzylkonium chloride and sodium dioctyl sulphosuccinate can be used to prepare the two phase liquid aqueous system from which the coacervate phase of the system, necessary to this invention is separated. Sodium dioctyl sulphosuccinate is the preferred surfactant. If it is desired, the two phase coacervate system can also be made without the use of surfactants. Under appropriate conditions and using appropriate procedures other substances such as acacia and gelatin complexes can be substituted for the surfactant component.

In the applicant's prior disclosure, the use of iodine and urea were disclosed as the active agents. In the present application, the inventor shows that iodine, iodophores and/or urea or combinations thereof can be dissolved in the previously referred to coacervate phase to prepare the claimed compositions of matter.

This invention consists of a method of preparing a composition of matter with powerful antiseptic, germicidal, bacteriacidal, fungicidal and viricidal properties; said method is comprised of the following steps:

(1) preparing a two phase liquid aqueous system wherein one phase of which is a lipoidal, non polar, liquid aqueous phase, herein also referred to as the coacervate phase and wherein the second phase is an equilibrium water phase; and (2) separating the coacervate phase from the equilibrium water phase; and (3) dissolving the appropriate quantity of the active agent in the coacervate phase; wherein the active agent is selected from the group consisting of iodine, urea, iodophores and combinations thereof.

As incorporated in this invention, iodine in either crystalline or liquid form or as a part of an organic molecule, e.g. povidone iodine may be used. Other methods of manufacture are also claimed. Alternatively, the manufacturing procedure provides, if desired, the optional step of adding dissolved urea to the product of Step (1). The urea will partition in roughly equal proportions between the two phases of liquid aqueous system referred to above. After the separating step is completed, the equilibrium water phase may be discarded. The composition obtained after the final step described above is completed is titrated to the desired pH by the dropwise addition of hydrochloric acid. By means of this procedure, any pH in the range of 3.5 to 7.5 may be produced.

GENERAL METHOD OF PREPARATION

To prepare the preferred version of the necessary two phase liquid aqueous system, disperse 5 to 15% weight to volume of sodium dioctyl sulphosuccinate in distilled water. Next, add that amount of sodium chloride so that the final concentration of the sodium chloride will range from 0.5 to 40% weight to volume. Following this addition, if desired, 5 to 40% weight to volume of urea is added.

Store the mixture described above, undisturbed, at for from one to twenty four hours. At the end of the storage period, the composition will have separated into two layers. The upper layer comprises a substantially polar, equilibrium water phase of the two phase system; the upper layer comprises a substantially non polar coacervate phase of the system. Separate the two phases by means of a separatory funnel or other appropriate means and discard the equilibrium water layer. If either iodine or an iodophore is to be used as the active agent, add that amount of either iodine or iodophore as will result in a finished product that will contain ½ to 1% molecular iodine. If an iodophore is used to prepare the claimed composition(s) povidone iodine is the preferred compound.

If the claimed composition is based on the combination of the coacervate phase described previously and urea, (i.e. without iodine or iodophore,) then 10 to 40% weight to volume of urea is used.

A mixing step is involved in the preparation of all of the claimed compositions. This step follows the combination of all the necessary ingredients and involves stirring the composition by means of a vortex mixer or other suitable means for from 12 to 24 hours. The mixing step is completed when a clear solution is achieved.

Titration of the composition(s) follows the mixing step and is accomplished by the dropwise addition of hydrochloric acid until the desired pH within the range of 3.5 to 7.5 is reached.

EXAMPLES

The claimed composition(s) may be embodied by means of any of the examples described below:

EXAMPLE 1

Ten percent weight to volume of sodium di (2 ethyexyl) sulfosuccinate was dispersed in 1000 mls of distilled water which contained 3% weight to volume of urea dissolved in distilled water. A solution of 1.8% sodium chloride was added to this mixture until oil like droplets began to form and settle to the bottom of the flask. This event marked the beginning of the formation of the two phase liquid aqueous system. The process of droplet formation and settling was allowed to proceed until no further settling was observed and no change in the volumes of each of the two phases was observed. The next step consisted of separating the two phases by means of a separatory funnel and discarding the equilibrium water phase. To 100 mls of the remaining coacervate phase, 1 gram of crystalline iodine was added and using a vortex mixer, the solution was thoroughly mixed for twelve hours at room temperature. The iodine was observed to have been completely dissolved by the end of the stirring step. The solution was then titrated to a pH of 6.5 by the dropwise addition of the necessary amount of dilute hydrochloric acid. The preparation was now completed and was then placed in glass containers at room temperature for storage.

EXAMPLE 2

The procedure of Example 2 followed that of Example 1 except that two grams of crystalline iodine was added to 100 mls of the coacervate phase and no urea was embodied in this Example.

EXAMPLE 3

10% weight to volume of sodium di (2 ethylexyl) sulphosuccinate was dispersed in 100 mls of distilled water which contained 3% weight to volume of urea dissolved in distilled water. A solution of 3% sodium chloride was added drop by drop to this mixture until oil like droplets began to form and settle to the bottom of the flask. The rest of the procedure followed that of Example 2 except that povidone iodine was used in place of crystalline iodine and was added to the coacervate phase in an amount that resulted in a finished product that contained 1% iodine. The solution was mixed at room temperature for twelve hours and titrated to a pH of 7.0 by the dropwise addition of hydrochloric acid.

EXAMPLE 4

The procedure of Example 4 followed that of Example 1 except that neither iodine nor an iodophore was used. In place of these components, 25% weight to volume of urea was used.

EXAMPLE 5

The procedure of Example 3 was followed except that the step in which urea is added, is omitted.

The examples of embodiments of the claimed invention which have been described immediately above, contain many specifications. These specifications should not be construed as limitations on the scope of the invention but rather as exemplifications of preferred embodiments. Many other desireable variations are possible. Accordingly, the scope of this invention should not be determined by the described embodiments but by the appended claims and their scientific equivalents.

SUMMARY

This invention pertains to closely related compositions of matter which possess powerful germicidal, antiseptic, bacteriacidal, fungicidal and viricidal properties and to methods of making these compositions. The method of manufacture of this invention uses the lipoidal, non polar liquid aqueous phase (i.e. the coacervate phase) of a two phase liquid aqueous system to incorporate iodine or iodine based preparations such as iodophores through the process of dissolution and optionally may incorporate urea. If desired, urea may be used in place of the iodine and/or iodophore component of this invention. The disclosed compositions are unusually stable, possess desireable vapor pressures and interfacial tensions, and are highly effective against a broad array of pathogenic micro-organisms. The claimed compositions are stable and germicidally active across a range of pH values extending from 3.4 to 7.5 in contrast to the iodine preparations now in common use (i.e. the iodophores) which must be manufactured to a pH of 3.0 to 4.0.

What I claim and desire to protect by Letters Patent:

1. A method of preparing a composition of matter which possesses antiseptic, bacteriacidal, germicidal fungicidal and viricidal properties and which comprises the following steps:
   (a) preparing a two phase liquid aqueous system wherein one phase is a lipoidal, non polar liquid aqueous phase, herein also referred to as the coacervate phase and the second phase is an equilibrium water phase;
   (b) separating the coacervate phase from the equilibrium water phase; and
   (c) dissolving an agent effective against pathogenic micro-organisms in the coacervate phase; wherein the agent is selected from the group consisting of iodine in either crystalline or liquid form, iodophores and urea.

2. The method of claim 1 which comprises the additional step of adding urea to the two phase liquid aqueous system and wherein the active agent is selected from the group consisting of iodine in crystalline or liquid form and iodophores.

3. The method of claim 1 wherein the two phase liquid aqueous system is prepared by using a surface active agent.

4. The method of claim 1 wherein the two phase liquid aqueous system is prepared by using a component selected from the group consisting of acacia and gelatin complexes.

5. The method of claim 1 wherein the two phase liquid aqueous system is prepared by using from 1 to 10% of a surfactant.

6. The method of claim 1 wherein the product of step (c) can range in pH from 3.4 to 7.5.

7. The method of claim 3 wherein the surfactant used is selected from the group consisting of benzylknoium chloride and sodium dioctyl sulphosuccinate.

8. A composition of matter prepared according to the method of claim 1 which is useful as an antiseptic, germicide, bacteriacide, fungicide and viricide.

* * * * *